(12) United States Patent
Chen et al.

(10) Patent No.: US 11,399,870 B2
(45) Date of Patent: Aug. 2, 2022

(54) AUTOMATIC TRACTION DEVICE FOR LOWER LIMB FRACTURE OSTEOSYNTHESIS

(71) Applicants: The Third Hospital of Hebei Medical University, Shijiazhuang (CN); Qi Zhang, Shijiazhuang (CN); Zhiyong Hou, Shijiazhuang (CN)

(72) Inventors: Wei Chen, Shijiazhuang (CN); Qi Zhang, Shijiazhuang (CN); Hongzhi Lv, Shijiazhuang (CN); Yingze Zhang, Shijiazhuang (CN); Zhiyong Hou, Shijiazhuang (CN); Yanbin Zhu, Shijiazhuang (CN); Xin Xing, Shijiazhuang (CN); Huijie Li, Shijiazhuang (CN); Dongwei Sun, Shijiazhuang (CN); Xiaodong Lian, Shijiazhuang (CN); Lin Jin, Shijiazhuang (CN); Lijie Ma, Shijiazhuang (CN)

(73) Assignees: The Third Hospital of Hebei Medical University, Shijiazhuang (CN); Qi Zhang, Shijiazhuang (CN); Zhiyong Hou, Shijiazhuang (CN)

( * ) Notice: Subject to any disclaimer, the term of this patent is extended or adjusted under 35 U.S.C. 154(b) by 180 days.

(21) Appl. No.: 16/936,720

(22) Filed: Jul. 23, 2020

(65) Prior Publication Data
US 2021/0196323 A1 Jul. 1, 2021

(30) Foreign Application Priority Data
Dec. 31, 2019 (CN) .......................... 201911423627.7
Dec. 31, 2019 (CN) .......................... 201922489153.8

(51) Int. Cl.
*A61B 17/64* (2006.01)
*A61B 17/00* (2006.01)

(52) U.S. Cl.
CPC ........ *A61B 17/6408* (2013.01); *A61B 17/645* (2013.01); *A61B 17/6416* (2013.01);
(Continued)

(58) Field of Classification Search
CPC ............ A61B 17/6408; A61B 17/6416; A61B 17/645; A61B 17/66; A61B 17/6425; A61B 2017/00991
(Continued)

(56) References Cited

U.S. PATENT DOCUMENTS 2,346,346 A * 4/1944 Anderson .......... A61B 17/6441
606/56
2,406,987 A * 9/1946 Anderson .......... A61B 17/6441
606/59
(Continued)

*Primary Examiner* — Eduardo C Robert
*Assistant Examiner* — David C Comstock
(74) *Attorney, Agent, or Firm* — Qinghong Xu

(57) ABSTRACT

An automatic traction device for a lower limb fracture osteosynthesis includes a chassis structure, a lower leg supporting structure and an upper leg supporting structure connected two by two. The automatic traction device further includes a tibia distal position adjusting device, for adjusting a position and an angle of a distal end of a tibia, on the lower leg supporting structure and close to the first end portion of the lower leg supporting structure; and a tibia proximal position adjusting device, for adjusting a position and an angle of a proximal end of a tibia, on the lower leg supporting structure and close to the second end portion of the lower leg supporting structure.

17 Claims, 4 Drawing Sheets

US 11,399,870 B2

Page 2

(52) U.S. Cl.
CPC ............... *A61B 2017/00398* (2013.01); *A61B 2017/00991* (2013.01)

(58) Field of Classification Search
USPC ........................................ 606/54, 57, 58, 59
See application file for complete search history.

(56) References Cited

U.S. PATENT DOCUMENTS

| | | | | |
|---|---|---|---|---|
| 3,135,257 | A * | 6/1964 | Anderson | A61G 13/0036 |
| | | | | 602/39 |
| 3,417,748 | A * | 12/1968 | Bimler | A61F 5/0585 |
| | | | | 602/34 |
| 5,160,335 | A * | 11/1992 | Wagenknecht | A61B 17/6466 |
| | | | | 606/57 |
| 5,180,380 | A * | 1/1993 | Pursley | A61B 17/60 |
| | | | | 606/56 |
| 7,947,862 | B2 * | 5/2011 | Livorsi | A61B 17/1764 |
| | | | | 5/624 |
| 9,056,042 | B2 * | 6/2015 | Russell | A61G 13/124 |
| 9,314,272 | B1 * | 4/2016 | DeMayo | A61G 13/0036 |
| 2004/0015114 | A1 * | 1/2004 | Hay | A61F 5/04 |
| | | | | 602/32 |
| 2019/0282274 | A1 * | 9/2019 | Singh | A61B 17/645 |

* cited by examiner

AUTOMATIC TRACTION DEVICE FOR LOWER LIMB FRACTURE OSTEOSYNTHESIS

CROSS REFERENCE

This application is based upon and claims priority to Chinese Patent Application No. 201922489153.8, filed on Dec. 31, 2019; and No. 201911423627.7, filed on Dec. 31, 2019, the entire contents thereof are incorporated herein by reference.

TECHNICAL FIELD

This disclosure relates to the technical field of orthopedic medical instruments, in particular to an automatic traction device for lower limb fracture osteosynthesis, which is suitable for osteosynthesis of femur and tibia intramedullary nailing implantation and percutaneous bone plate implantation.

BACKGROUND

Femur and tibia fractures are common clinical fractures. It is difficult to reposition the tibia fracture and restore the length of the tibia fracture during operation due to occurrence of shortening deformity by pulling muscle after fracture of a patient's tibia, because of the strong leg muscle strength. If anatomical reduction is not successful during operation, complications such as malunion and poor lower limb force line may occur after operation, and thus lead to traumatic arthritis or osteoarthritis, and even seriously affect the patient's limb function and life quality.

Intramedullary nail fixation or minimally invasive percutaneous plate implantation is the common treatment for the femur and tibia fractures. Traction in the operation is an important means to reduce the femur and tibia fractures and restore the length of lower limb. Now, there are generally two assistants need to help traction of the patient as implanting intramedullary nails or performing minimally invasive percutaneous bone plates, and the two assistants hold a proximal end and a distal end of fractured bones respectively to reposition the femur or the tibia. However, this method often cannot stably maintain fracture reduction and the length of the lower limb, so that the reduction effect is not ideal, thus affecting the treatment effect. Moreover, the two assistants would occupy the space of the operator and affect the operation of the operator.

The traction devices are used to reduce the fractured femur or tibia so as to overcome the above problems. However, it is required to straight the lower limb out in the existing traction devices. It is required that intramedullary nails are implanted from the femur distal end or the tibia proximal end, so that an operation can be made under the condition of keeping the patient's leg bent.

SUMMARY

According to one aspect of the present disclosure, an automatic traction device for a lower limb fracture osteosynthesis, including:
- a chassis structure, having a first end portion and a second end portion opposite to each other;
- a lower leg supporting structure, having a first end portion and a second end portion opposite to each other, wherein the first end portion of the lower leg supporting structure 300 is connected to the first end portion of the chassis structure;
- an upper leg supporting structure, having a first end portion and a second end portion opposite to each other, wherein the first end portion of the upper leg supporting structure is connected to the second end portion of the chassis structure, and the second end portion of the upper leg supporting structure is connected to the second end portion of the lower leg supporting structure;
- a tibia distal position adjusting device, for adjusting a position and an angle of a distal end of a tibia, on the lower leg supporting structure and close to the first end portion of the lower leg supporting structure; and
- a tibia proximal position adjusting device, for adjusting a position and an angle of a proximal end of a tibia, on the lower leg supporting structure and close to the second end portion of the lower leg supporting structure.

According to another aspect of the present disclosure, an automatic traction device for a lower limb fracture osteosynthesis, including:
- a support frame that is in a triangular structure and used for supporting a patient's lower limb to form and maintain a state of bending the leg, wherein the support frame includes a chassis structure that is horizontally arranged, a upper leg supporting structure and a lower leg supporting structure which are arranged back to one another and at both end portions of the chassis structure; the end portions of the adjacent faces are hinged with each other, and length of the faces is able to be adjusted and locked by means of an edge adjusting mechanism;
- a tibia K-wire (Kirschner wire) installation, which has two tibia K-wire mounting structures respectively arranged on both sides of the lower leg supporting structure and is used for securing to the both ends of a first K-wires which passes through a heel bone or a tibia distal end of the patient, and on the first K-wire is provided a first traction bow; and
- two femur K-wire installations, which are arranged in parallel and at equal intervals; wherein each of the femur K-wire installations has two femur K-wire mounting structures respectively arranged on both sides of the upper leg supporting structure; each of the femur K-wire installations is used for securing to both ends of a second K-wire that passes through a femur distal end of the patient; and on each of the two second K-wires is provided a second traction bow;

wherein the lower leg supporting structure includes two first supporting pipes that are respectively arranged on both sides of the lower leg supporting structure along a length direction of the lower leg supporting structure; and a supporting plate between the two first supporting pipes, for supporting the tibia distal end; the edge adjusting mechanism synchronously extends and retracts the two first supporting pipes through an automatic or manual driving structure so as to realize the length adjustment of the lower leg supporting structure; the upper leg supporting structure includes two second supporting rods that are respectively arranged on both sides of the upper leg supporting structure along a length direction of the upper leg supporting structure; and the edge adjusting mechanism synchronously extends and retracts the two second supporting rods through an automatic or manual driving structure so as to realize the length adjustment of the upper leg supporting structure; a second transverse bar is further included, wherein the second transverse bar is located at an intersection of the upper leg supporting structure and the lower leg supporting structure.

Wherein it is also provided with a first lifting mechanism for driving the tibia K-wire mounting structure to move up and down along the lower leg supporting structure and to be locked.

Wherein the first lifting mechanism includes two first lifting parts which are respectively arranged on each of the first supporting pipes and are connected with a corresponding one of the tibia K-wire mounting structures through universal ball joints; and the two first lifting parts are able to be driven individually to make the tibia K-wire mounting structure on the corresponding side to be movable along the first supporting pipe and to be locked; and the two first lifting parts are also able be driven simultaneously.

Wherein each of the first lifting parts includes a first nut which is rotatably connected with the corresponding one of the tibia K-wire mounting structures in a parallel plane of the lower leg supporting structure by means of the universal ball joint; and a first driving part for driving the first nut to move along the direction of the first supporting pipe.

Wherein the first driving part is driven by a lead screw nut or a telescopic rod; the first driving part includes a first lead screw rotatably connected to a lower end of the first supporting pipe; a first motor connected with a lower end of the first lead screw and hinged with the chassis structure, and the first nut is threadedly connected with the first lead screw; or
 a first electric push rod that is arranged in parallel with the first supporting pipe and secured to the lower leg supporting structure; wherein a telescopic end of the first electric push rod is secured to the first nut; the first nut is slidably sleeved on the corresponding first supporting pipe.

Wherein it is also provided with a first distance adjusting mechanism for driving the tibia K-wire mounting structure to move close to or away from the lower leg supporting structure.

Wherein the first distance adjusting mechanism includes two first distance adjusting devices that are arranged perpendicular to the lower leg supporting structure and are respectively arranged between two first nuts and the universal ball joints; and the two first lifting parts are able to be driven individually to make the tibia K-wire mounting structure on the corresponding side to be movable along the first supporting pipe and to be locked; and the two first lifting parts are also able be driven simultaneously.

Wherein a tibia proximal position adjusting device includes at least one first jacking assembly that is arranged at a longitudinal centerline position of the lower leg supporting structure; at least two first lateral pressing assemblies that are respectively arranged on both sides of the lower leg supporting structure; and a binding band having one end secured to a first supporting pipe; and the other end detachably secured to another first supporting pipe, or is detachably secured to an original first supporting pipe after being folded around the other first supporting pipe; and the length of the binding band around the patient's lower leg is adjustable.

Wherein the first jacking assembly includes a lower leg fixing plate with an inward concave radian, and having two ends connected with corresponding first supporting pipes; and a third electric push rod fixed at the middle of the lower leg fixing plate, and having a telescopic end that protrudes from the lower leg fixing plate, and is secured to a top pressing plate.

Wherein the first jacking assembly further includes a second driving part for driving the lower leg fixing plate to be slidable along the first supporting pipe and to be locked.

Wherein the first lateral pressing assembly includes two first sliding seats that are respectively arranged on two first supporting pipes and are slidably connected with the first supporting pipes; a first passive telescopic part that is arranged transversely along the lower leg supporting structure and fixed on a first sliding seat, and the first passive telescopic part including a rod body and a pipe body which is slidingly sleeved with the rod body; a first active telescopic part that is arranged transversely along the lower leg supporting structure and fixed on the other first sliding seat, and has the telescopic end facing towards the first passive telescopic part; and a first linkage plate that has an inward concave radian, wherein two ends of the first linkage plate are turned out to form a connecting part, and a protruding end of the first passive telescopic part and a telescopic end of the first active telescopic part pass through the connecting part and are secured to the connecting part; on the ends of the first passive telescopic part and the first active telescopic part opposite to each other are fixed lateral pressing plates.

Wherein the first active telescopic part is driven by a screw nut or a telescopic rod, and includes:
 a second lead screw arranged transversely along the lower leg supporting structure, wherein the outer end of the second lead screw is connected with a second motor secured to another first sliding seat; and a first threaded sleeve threadedly connected with the other end of the second lead screw and passing through and secured to the corresponding connecting part; or
 a fourth electric push rod arranged transversely along the lower leg supporting structure and fixed on the other first sliding seat, wherein a telescopic end of the fourth electric push rod passes through and is secured to the corresponding connecting part 571.

Wherein the first lateral pressing assembly further includes a third driving part for driving the first linkage plate to be slidable along the first supporting pipe and to be locked.

Wherein it is also provided with a second lifting mechanism for driving the two femur K-wire installations to move up and down along the upper leg supporting structure synchronously and to be locked.

Wherein the second lifting mechanism includes two second lifting parts that are respectively arranged on the second supporting rods and connected with the corresponding femur K-wire mounting structure through the universal ball joints, and the two second lifting parts are able to be driven individually to make the tibia K-wire mounting structure on the corresponding side to be movable along the second supporting pipe and to be locked; and the two second lifting parts are also able be driven simultaneously.

Wherein each of the second lifting parts includes a lifting arm that is arranged in parallel with the second supporting rod and positioned at an upper end of the second supporting rod; a fourth driving part for driving the lifting arm to move up and down along the second supporting rod and to be locked; a connecting arm that is arranged at an angle with the lifting arm and connected with the upper end of the lifting arm; and a mounting sleeve that is sleeved on the connecting arm; the two femur K-wire installations are arranged along a length direction of the connecting arm, and the femur K-wire mounting structure is connected to the mounting sleeve by means of the universal ball joint.

Wherein the fourth driving part is driven by a lead screw nut or a telescopic rod, and includes a fourth lead screw that is arranged in parallel with the lifting arm, and has a lower end connected with a third motor secured to the second supporting rod; and a second sliding block secured to the lifting arm and threadedly connected with the fourth lead screw; or
- a sixth electric push rod that is arranged in parallel with the lifting arm and secured to the second supporting rod, and has a telescopic end secured to the lifting arm.

Wherein a second distance adjusting mechanism is also provided and is used for driving the femur K-wire mounting structure to move close to or away from the upper leg supporting structure along the connecting arm.

Wherein the second distance adjusting mechanism includes two automatic telescopic parts, each of the automatic telescopic parts is arranged along a direction of the connecting arm and secured to the connecting arm, and the two automatic telescopic parts are able to be driven individually so that the mounting sleeve slides along the connecting arm on the corresponding side, and the two automatic telescopic parts are also able to be driven simultaneously.

Wherein it is also provided with a femur fracture anterior-posterior angulation adjusting mechanism. The femur fracture anterior-posterior angulation adjusting mechanism may correct angulation deformity before and after femur fracture by adjusting an angle between the connecting arm and the lifting arm.

Wherein the femur fracture anterior-posterior angulation adjusting mechanism includes two fifth driving parts that are respectively arranged at free ends of the two connecting arms and used for driving the connecting arms to rotate along a position where the connecting arms are hinged with the lifting arms.

Wherein each of the fifth driving parts is driven by a lead screw nut or a telescopic rod. The fifth driving part includes: a fifth lead screw which forms a triangle with the connecting arm and the lifting arm, and has a lower end connected with a fourth motor hinged with the upper leg supporting structure; a second threaded sleeve which is threadly connected to the upper end of the fifth lead screw, wherein the upper end of the second threaded sleeve is hinged with the free end of the connecting arm; or
- an eighth electric push rod, which forms a triangle with the connecting arm and the lifting arm, and has a lower end hinged with the leg supporting structure and an upper end hinged with the free end of the connecting arm.

Wherein it is also provided with a femur fracture reduction mechanism. The femur fracture reduction mechanism includes at least one second jacking assembly that is arranged at a longitudinal centerline position of the upper leg supporting structure; and at least two second lateral pressing assemblies that are respectively arranged on both sides of the upper leg supporting structure.

Wherein the second jacking assembly includes a upper leg fixing plate with an inward concave radian, and having two ends slidably connected with a corresponding one of the second supporting rods; and a ninth electric push rod, which is fixed at the middle of the upper leg fixing plate, and has a telescopic end protruding from the upper leg fixing plate and is secured to a top pressing plate.

Wherein the second jacking assembly further includes a sixth driving part for driving the upper leg fixing plate to be slidable along the second supporting rod and to be locked.

Wherein the second lateral pressing assembly includes two second sliding seats, which are respectively arranged on the two second supporting rods and are slidably connected with the second supporting rods; a second passive telescopic part, which is arranged transversely along the upper leg supporting structure and fixed on a second sliding seat, the second passive telescopic pail including a rod body and a pipe body slidingly sleeved with the rod body; a second active telescopic part, which is arranged transversely along the upper leg supporting structure and fixed on another second sliding seat, and the telescopic end of the second active telescopic part facing towards the second passive telescopic part; and a second linkage plate, with an inward concave radian, and two ends of the second linkage plate being turned out to form a connecting part; wherein the protruding end of the second passive telescopic part and the telescopic end of the second dynamic telescopic part both pass through and are secured to the connecting part; and on the ends of the second passive telescopic part and the second active telescopic part opposite to each other are secured lateral pressing plates.

Wherein the second active telescopic part is driven by a lead screw nut or a telescopic rod; the second active telescopic part includes a fifth lead screw; which is transversely arranged along the upper leg supporting structure and has an outer end connected with a fifth motor that is secured to another second sliding seat; and a third threaded sleeve, which is threadedly connected with the other end of the fifth lead screw and is secured to the fifth lead screw through the corresponding connecting part; or
- an eleventh electric push rod, which is arranged transversely along the upper leg supporting structure and secured to the other second sliding seat, the telescopic end of the eleventh electric push rod passes through the corresponding connecting part.

Wherein the second lateral pressing assembly further includes a seventh driving part for driving the second sliding seat to be slidable along the second supporting rod and to be locked.

BRIEF DESCRIPTION OF THE DRAWINGS

Hereinafter, the present disclosure will be further described in detail with reference to the drawings and specific embodiments.

DETAILED DESCRIPTION

Hereinafter, the technical solutions in the embodiments of the present disclosure writ, be clearly and completely described in combination with the accompanying drawings. Obviously, the embodiments as described are merely a part of the embodiments, but not all of the embodiments of the present disclosure. Other embodiments obtained by the person skilled in the art without any creative effort are within the scope of the present disclosure.

In order to understand the disclosure fully, many specific details are set forth in the following description, besides other implementation that are different from those described herein may be adopted, that is, those skilled in the art could make similar modification without violation of the present disclosure. The present disclosure therefore is not limited to the specific embodiments below.

Chinese patent application for an invention (CN201910832613.4) discloses a lower limb traction device for an intramedullary nailing operation capable of keeping the patient's leg bent during operation; however this lower limb traction device for the intramedullary nailing operation at least has disadvantages below.

As the device has a low stability, when a total height of the device is adjusted depending on four jacking bolts on the bottom if a leg-bending angle is unchanged, it is difficult to adjust the four jacking bolts synchronously, and it is easy to cause decline of the whole device;

The whole device is supported only by the four jacking bolts and placed on the operating bed. The device cannot be placed stably because the surface of the operating bed has a certain deformability, so that there is shaking or jacking bolts sinking in the operation process to decline the device, so as to affect accuracy of traction reduction, and thus affect the smooth operation.

The surgery operation will be affected due to that a traction bow at the tibia is arranged at an end of the device in a length direction, taking up space.

Since various adjustment of the traction device during operation is manual adjustment, operation difficulty of the operator is increased and operation time is prolonged.

In the lower limb traction device, as the lead screw is rotationally connected with a bow back of the traction bow, difference between the two ends of the K-wire and the lower leg supporting plate or the upper leg supporting plate cannot be adjusted, that is, a pronation angle or a valgus angle of the fractured bone cannot be corrected, thereby cannot realizing reduction of the fractured bone in any direction and having a blind area for use.

Figure 1:
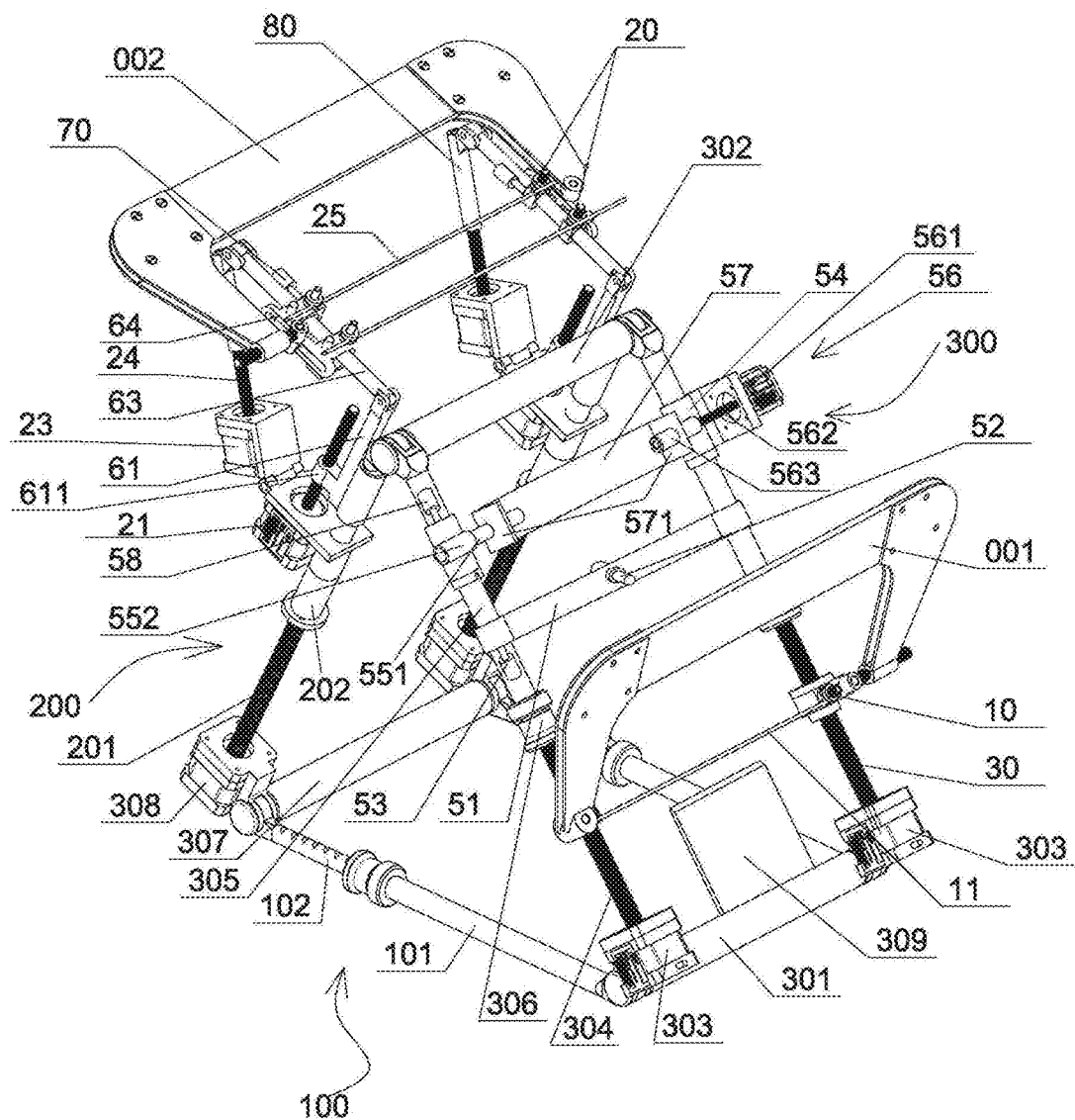
FIG. 1 is a schematic view of a three-dimensional structure of an automatic traction device for a lower limb fracture osteosynthesis of the present disclosure (the femur fracture reduction mechanism is not shown, but has the same structure as the tibia proximal position adjusting device)
Figure 2:
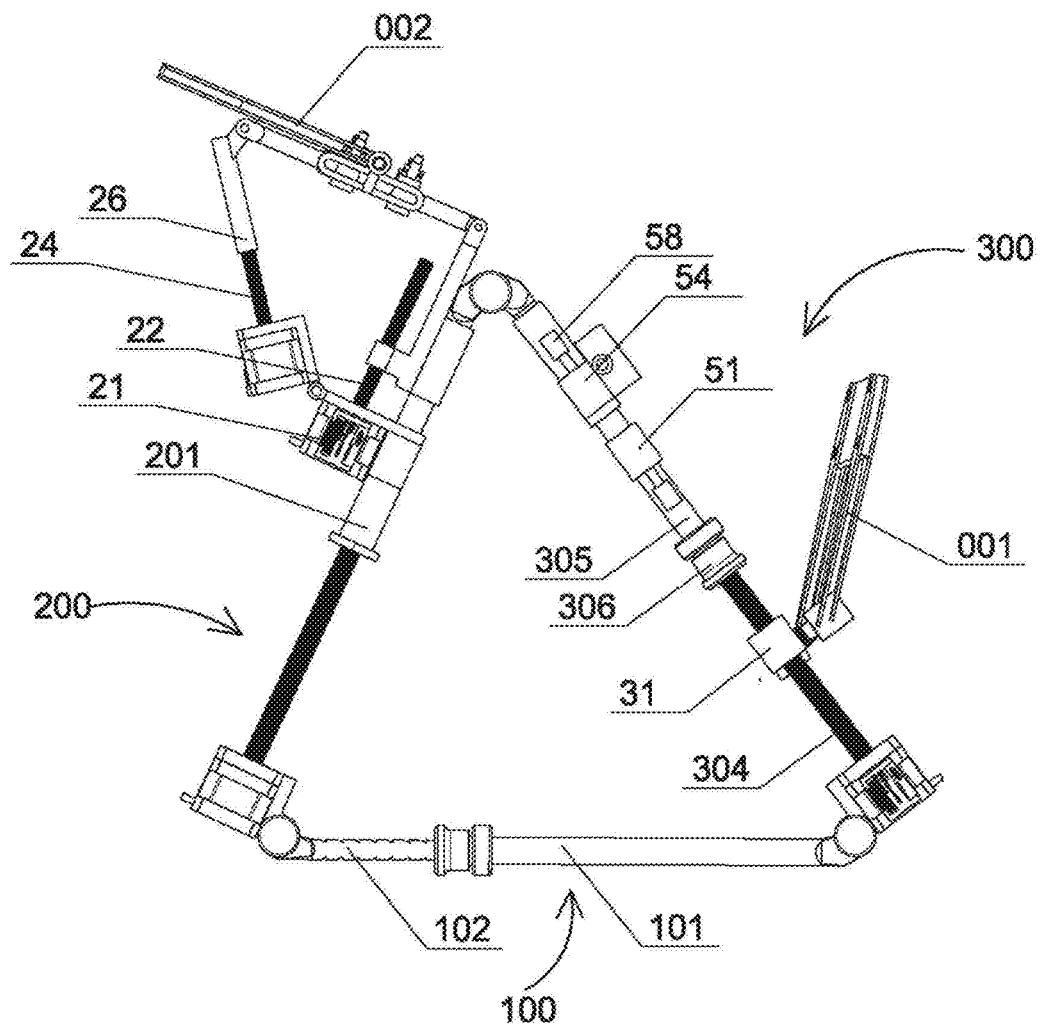
FIG. 2 is a schematic side view of FIG. 1.
Figure 3:
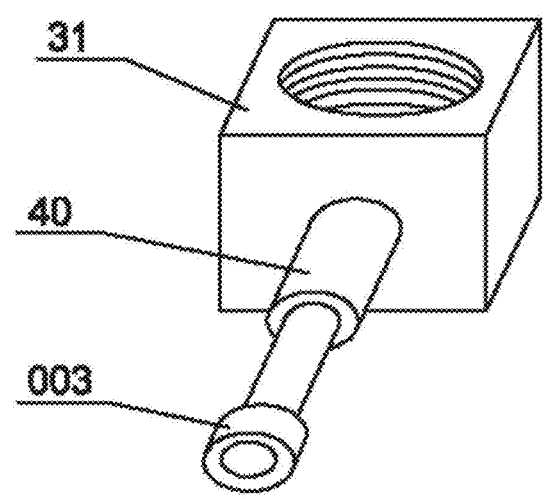
FIG. 3 is a schematic view of an installation structure of a first distance adjusting device of the present disclosure.

As shown in FIG. 1 to FIG. 3, in an embodiment of present disclosure, the automatic traction device for a lower limb fracture osteosynthesis includes a support frame, a tibia proximal position adjusting device, a tibia distal position adjusting device (i.e., a tibia K-wire installation) and a femur position adjusting device (i.e., a femur K-wire installation).

The support frame may be made of carbon fiber to avoid affecting fluoroscopy effect during operation. The support frame has a triangular structure and includes a chassis structure 100 that is horizontally arranged, an upper leg supporting structure 200 and a lower leg supporting structure 300 which are arranged back to one another and at both end portions of the chassis structure 100.

A chassis structure 100 has a first end portion and a second end portion opposite to each other. A lower leg supporting structure 300 has a first end portion and a second end portion opposite to each other, wherein the first end portion of the lower leg supporting structure 300 is connected to the first end portion of the chassis structure. An upper leg supporting structure 200 has a first end portion and a second end portion opposite to each other, wherein the first end portion of the upper leg supporting structure 200 is connected to the second end portion of the chassis structure, and the second end portion of the upper leg supporting structure 200 is connected to the second end portion of the lower leg supporting structure 300;

In an embodiment, the chassis structure 100 is a telescopic structure; the upper leg supporting structure 200 is a telescopic structure; the lower leg supporting structure 300 is a telescopic structure; the lower leg supporting structure 300 is rotatably connected to the chassis structure 100; the lower leg supporting structure 300 is rotatably connected to the upper leg supporting structure 200; and the upper leg supporting structure 200 is rotatably connected to the chassis structure 100.

Specifically, the lower leg supporting structure 300 includes: a first transverse bar 301 and a second transverse bar 302 parallel to each other; and two first longitudinal assemblies connected between the first transverse bar 301 and the second transverse bar 302 and parallel to each other, and each of the first longitudinal assemblies has a telescopic structure.

Each of the first longitudinal assemblies includes: a first motor 303 hinged on the first transverse bar 301; a first lead screw 304 driven by the first motor 303; a first supporting pipe 305 having one end connected to the second transverse bar 302 and the other end sleeved on the first lead screw 304; and a first locking member 306 on the first supporting pipe 305, for locking the first lead screw 304 and the first locking member 306.

The upper leg supporting structure 200 includes: a third transverse bar 307 parallel to the first transverse bar 301; and two second longitudinal assemblies connected between the third transverse bar 307 and the first transverse bar 301 and parallel to each other, wherein each of the second longitudinal assemblies has a telescopic structure.

Each of the second longitudinal assemblies includes: a third motor 308 on the third transverse bar 307; a third lead screw 201 driven by the third motor 308; and a second supporting pipe 202 having one end connected to the second transverse bar 302, and the other end sleeved on the third lead screw 201, wherein an inner surface of the second supporting pipe 202 has threads matched with the third lead screw 201. A locking member for further locking the third lead screw 201 and the second supporting pipe 202 may be further provided.

In an embodiment, the automatic traction device further includes a second lifting mechanism on the upper leg supporting structure 200 and lifting relative to the upper leg supporting structure 200.

The second lifting mechanism includes: two fourth motors 21 respectively on the two second supporting pipes 202; two fourth lead screws 22 respectively driven by the two fourth motors 21; two lifting arms 61 slidably disposed on the two second supporting pipes 202, respectively, wherein a nut 611 matched with the fourth lead screw 22 is provided at a lower end portion of the lifting arm 61.

Furthermore, the second lifting mechanism further includes: two connecting arms 63 with end portions respectively hinged to the upper end portions of the two lifting arms 61, wherein the two fourth lead screws 22 are parallel to the two second supporting pipes 202, the two lifting arms 61 are parallel to the two second supporting pipes 202; and the femur position adjusting device is arranged on the two connecting arms 63.

In an embodiment of the present disclosure, the automatic traction device further includes two fifth motors 23 respectively hinged to the two fourth motors 21; two fifth lead screw's 24 respectively driven by the two fifth motors 23;

wherein the end portions of the two fifth lead screws 24 are respectively hinged with the other end portions of the two connecting arms 63.

A tibia distal position adjusting device for adjusting a position and an angle of a distal end of a tibia is arranged on the tower leg supporting structure 300 and close to the first end portion of the lower leg supporting structure 300.

In an embodiment of the present disclosure, the tibia distal position adjusting device includes: two first nuts 31 respectively on the two first lead screws 304 and matched with the first lead screw's 304; two first distance adjusting devices 40 respectively on the two first nuts 31, wherein the first distance adjusting devices are perpendicular to the lower leg supporting structure 300; two universal ball joints 003 respectively on the two first distance adjusting devices 40; two tibia K-wire mounting structures 10 respectively on the two universal ball joints; and a first K-wire 11 between the two tibia K-wire mounting structures 10, and on the first K-wire being provided a first traction bow 001; wherein the two first distance adjusting devices are used to adjust a distance between the first K-wire 11 and the lower leg supporting structure 300.

The tibia proximal position adjusting device for adjusting a position and an angle of a proximal end of a tibia is arranged on the lower leg supporting structure 300 and close to the second end portion of the lower leg supporting structure 300.

In an embodiment of the present disclosure, the tibia proximal position adjusting device includes: two first sliding seats 54 slidably disposed on the two first supporting pipes 305; two third driving parts 58 respectively on the two first supporting pipes 305, for driving the first sliding seats 54 to be slidable along the first supporting pipes 305 and to be locked; a first passive telescopic part arranged transversely along the lower leg supporting structure 300 and fixed on one of the two first sliding seats 54; a first active telescopic part 56 arranged transversely along the lower leg supporting structure 300 and fixed on the other of the two first sliding seats 54; and a first linkage plate 57, having connecting parts 571 formed by bending on both end portions, wherein a protruding end of the first passive telescopic part and telescopic ends of the first active telescopic part 56 respectively penetrate through the two connecting parts 571 and are telescopic relative to the two connecting parts 571.

The first passive telescopic part includes: a pipe body 552 fixed on one of the two first sliding seats 54; and a rod body 551 sleeved within the pipe body 552 and being telescopic relative to the rod body 551, wherein one end of the rod body 551 is arranged through the connecting part 571.

The first active telescopic part 56 is driven by a lead screw nut, and the first active telescopic part 56 includes: a second motor 561 on the first sliding seat 54; a second lead screw 562 arranged transversely along the lower leg supporting structure 300 and driven by the second motor 561; a first threaded sleeve 563 threadedly fitted to the second lead screw and arranged through a corresponding one of the connecting parts 571; and a locking member at an end portion of the second lead screw, for locking the second lead screw and the connecting parts 571.

The first active telescopic part 56 is driven by a telescopic rod, and the first active telescopic part 56 includes: a fourth electric push rod arranged transversely along the lower leg supporting structure 300 and on the other of the first sliding seats 54, wherein a telescopic end of the fourth electric push rod is arranged through a corresponding one of the connecting parts 571; and a locking member at an end of the four electric push rod, for locking the four electric push rod and the connecting parts 571.

In an embodiment of the present disclosure, the tibia proximal position adjusting device further includes: two second distance adjusting devices respectively on the two first sliding seats 54 and between the first passive telescopic part and the first active telescopic part, wherein the second distance adjusting devices are perpendicular to the lower leg supporting structure 300 and used for adjusting distances between the first passive telescopic part, the first active telescopic part and the lower leg supporting structure 300. The second distance adjusting device may be an electric push rod or a lead screw driven by the motor.

In an embodiment of the present disclosure, the tibia proximal position adjusting device further includes: at least one first jacking assembly, each of the first jacking assemblies including: a lower leg fixing plate 51 with two ends respectively connected to the two first supporting pipes 305; and a third electric push rod 52 in the middle of the lower leg fixing plate 51, wherein the third electric push rod 52 extends and retracts in a direction perpendicular to the lower leg supporting structure 300.

In an embodiment of the present disclosure, both ends of the lower leg fixing plate 51 are slidably arranged on the two first supporting pipes 305, and the first jacking assembly further includes: a second driving part 53 for driving the lower leg fixing plate 51 to be slidable along the first supporting pipes 305 and to be locked.

In an embodiment of the present disclosure, a surface of the lower leg fixing plate 51 has a radian; a surface of the first linkage plate 57 has a radian; each of a protruding end of the third electric push rod 52, a protruding end of the first passive telescopic part and a protruding end of the first active telescopic part 56 is provided a top pressing plate.

A femur position adjusting device for adjusting a position and an angle of a femur is disposed on the upper leg supporting structure 200 and close to the second end portion of the upper leg supporting structure 200.

In an embodiment of the present disclosure, the femur position adjusting device includes: two mounting sleeves 64 slidably disposed on the two connecting arms 63, respectively; two automatic telescopic parts 70 respectively arranged on the two connecting arms 63, for driving the connecting arms 63 to be movable and locked; at least one pair of femur K-wire mounting structures 20, wherein each pair of femur K-wire mounting structures 20 are respectively provided on the two mounting sleeves 64, and between each pair of the femur K-wire mounting structures 20 is installed a second K-wire 25.

A tibia K-wire installation has two tibia K-wire mounting structures 10 respectively arranged on both sides of the lower leg supporting structure 300 and is used for securing to the both ends of a first K-wires which passes through a heel bone or a tibia distal end of the patient, and on the first K-wire 11 is provided a first traction bow 001; and Two femur K-wire installations are arranged in parallel and at equal intervals; wherein each of the femur K-wire installations has two femur K-wire mounting structures respectively arranged on both sides of the upper leg supporting structure 200; each of the femur K-wire installations is used for securing to both ends of a second K-wire 25 that passes through a femur distal end of the patient; and on each of the two second K-wires is provided a second traction bow 002.

Figure 4:
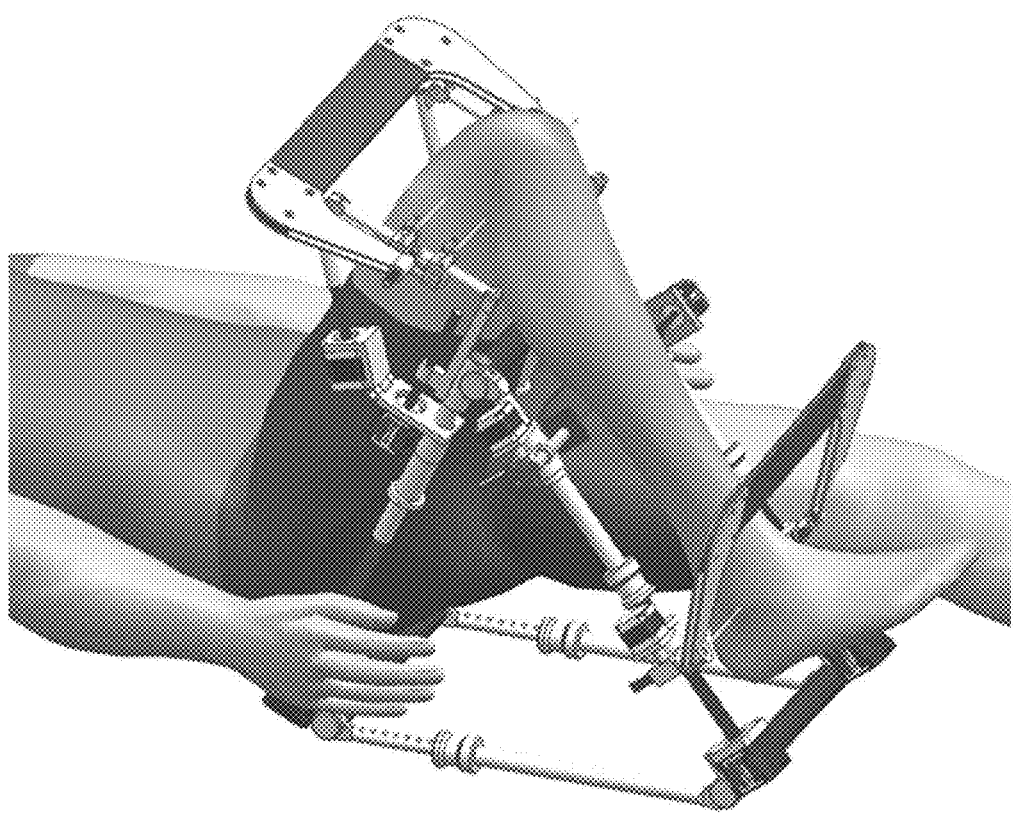
FIG. 4 is a use reference view of an automatic traction device for a tower limb fracture osteosynthesis.

As shown in FIG. 4, during operation, the automatic traction device is placed on an operating table and under a patient's lower limbs. The patient lays down, bending the lower limbs to be operated, resting an upper leg on the upper leg supporting structure 200 and resting a lower leg on the lower leg supporting structure 300, thus supporting the patient's lower limb to form and maintain in a bending state, so that it is easy for a doctor to perform an operation. In order to adapt to different postures of various patients, the support frame also has an adjustment function, specifically adjusting lengths of the chassis structure 100, the lower leg supporting structure 300, the upper leg supporting structure 200, and the size of the formed angle; as such the patient's upper leg can rest on the upper leg supporting structure 200 and the lower leg can rest on the lower leg supporting structure 300.

When the device is used to operate a heel bone or tibia distal fracture osteosynthesis, as an example of implanting intramedullary nails, the traction method includes following steps of:
  implanting a first K-wire 11 in a proper position under a perspective environment;
  applying proper transverse traction force to both ends of the first K-wire by using a first traction bow 001 to keep the first K-wire 11 in a linearly stretched state;
  securing the both ends of the first K-wire 11 to a tibia K-wire installation;
  adjusting a support frame to extend the lower leg supporting structure 300 downwardly, so as to drive the tibia distal position adjusting device to move downwardly, thereby applying a downward traction force to the first K-wire and reduce a fracture of a fractured bone;
  performing an intramedullary nailing operation.

When the device is used to operate a femur distal fracture osteosynthesis, as an example of implanting intramedullary nails, the traction method includes following steps of:
  implanting a second K-wire 25 respectively into front and back sides of the femur distal end under a perspective environment;
  applying a proper transverse traction force to both ends of the second K-wire 25 by using a second traction bow 002, to keep the second K-wire 25 in a linearly stretched state;
  securing the both ends of the second K-wire 25 to the femur position adjusting device;
  adjusting a support frame to extend the upper leg supporting structure 200 upwardly, so as to drive the femur position adjusting device to move upwardly, and thereby applying an upward traction force to the second K-wire and reduce the fracture of fractured bone;
  performing an intramedullary nailing operation.

Wherein the traction bow is an existing product, and the traction bow and the support frame have no connection structure and may be selectively used according to requirement for the operation.

The device may make the femur or tibia stable and maintained in a reduction state as required for implantation of intramedullary nails. Since the lengths of the chassis structure 100, the upper leg supporting structure 200 and the lower leg supporting structure 300 and the angles therebetween of the support frame may be adjustable, a posture of the support frame can be adjusted according to the patient's body shape to meet the different patient's needs. And, the tibia K-wire installation and the femur position adjusting device are configured not to protrude out of the support frame in a length direction, and thus do not occupy an operating space. In addition, as pulling the K-wire to reduce the fracture to restore the length of the lower limb, it is possible to realize pulling by adjusting the length of the corresponding face on the support frame without any external force. It is beneficial to improve quality and efficiency of the operation, and is suitable for popularization and application in various medical institutions.

According to an embodiment of the present disclosure, a further improvement may be made such that the lower leg supporting structure 300 and the upper leg supporting structure 200 have frame-type structures with hollow out middle portions to observe inside easily and reduce compression against the lower limb after being fasten.

Specifically, the lower leg supporting structure 300 includes two first longitudinal assemblies, which are respectively placed on both sides of the lower leg supporting structure 300 and arranged along a length direction of the lower leg supporting structure 300; a supporting plate 309 for supporting the tibia distal end on the first transverse bar 301 between the two first longitudinal assemblies. The edge adjustment mechanism enables the two first longitudinal assemblies to expand and retract synchronously through an automatic or manual driving structure to realize the length adjustment of the lower leg supporting structure 300. The upper leg supporting structure 200 includes two second longitudinal assemblies, which are respectively arranged on both sides of the upper leg supporting structure 200 and arranged along a length direction of the upper leg supporting structure 200. The edge adjusting mechanism extends and retracts the two second longitudinal assemblies synchronously through an automatic or manual driving structure to realize the length adjustment of the upper leg supporting structure 200.

The patient's lower limb rests on and bends over the second transverse bar 302, the supporting plate 309 is configured to support the distal end of the lower limb and has a radian fitted to the limb, so as to ensure the stability of the patient's bent legs and ensure the operation quality.

According to an embodiment of the present disclosure, the chassis structure 100 includes two third supporting assemblies, which are arranged along a length direction of the chassis structure 100 and are located on both sides of the chassis structure 100 in parallel. The third supporting assembly includes a third supporting pipe 101, a third connecting rod 102 that is telescopic relative to the third supporting pipe 101, and a third locking member 103, wherein one end of the third supporting pipe 101 is hinged to the first transverse bar 301, one end of the third connecting rod 102 is hinged to the third transverse bar 307, the other end of the third supporting pipe 101 is sleeved outside the other end of the third connecting rod 102, and the third locking member 103 is arranged outside the third supporting pipe 101, for locking the third supporting pipe 101 and the third connecting rod 102. On the third connecting rod 102 is provided a plurality of dents which facilitate for locking.

The adjustment of the lengths of the components in the support frame can be realized by expansion and retraction of the components, for example, by an electric push rod, a lead screw nut, automatic driving of an air cylinder and an oil cylinder or manual driving of a telescopic ratchet and the like.

According to an embodiment of the present disclosure, the two first nuts 31 move up and down on the first lead screw 304, thus constituting a first lifting mechanism for driving the tibia K-wire mounting structure 10 to move up and down along the lower leg supporting structure 300 and to be locked.

According to an embodiment of the present disclosure, the two first nuts 310 are able to be driven individually, to make the tibia K-wire mounting structure 10 on the corresponding side to be movable along the first lead screw 304 and to be locked, and the two first nuts 31 are also able be driven simultaneously.

As the tibia K-wire mounting structure 10 is secured to the first K-wire 11, since implantation angles of the first K-wire 11 are different, it is not necessary to implant in a transverse direction of the lower leg supporting structure 300. Therefore, when the two tibia K-wire mounting structures 10 are secured to the ends of the corresponding first K-wire 11, the two first nuts 31 are able be driven individually, so that the two tibia K-wire mounting structures 10 correspond to and are secured to both ends of the first K-wire 11.

After the tibia K-wire mounting structure 10 is secured to the first K-wire 11, when the tibia fracture has a lateral angulation deformity, the two first nuts 31 are able be driven individually to adjust relative height of the two ends of the first K-wire 11, thereby correcting lateral displacement of the distal fracture of the tibia to restore the fractured bone that has been displaced.

As the lower limb length is restored, the two first nuts 31 are also able be driven simultaneously to pull the first K-wire 11 to the tibia distal end, so as to reduce the fracture of the fractured bone and restore the length of the lower limb.

As above described, each of the first nuts 31 is rotatably connected with the corresponding tibia K-wire mounting structure 10 within a parallel plane of the lower leg supporting structure 300 by means of an universal ball joint 003. A first driving part drives the first nut 31 to move along the first lead screw 304.

According to an embodiment of the present disclosure, the first driving part is driven by a lead screw nut. The first driving part includes a first lead screw 304 rotatably connected to a lower end of a first supporting pipe 305 through a bearing; and a first motor 303 connected to a tower end of the first lead screw 304 and hinged with the chassis structure 100. The first nut 31 is threadedly connected to the first lead screw 304. The first nut 31 moves up and down along the first lead screw 304 by forward rotation or reverse rotation of the first motor 303.

According to an embodiment of the present disclosure, the first driving part is driven by a telescopic rod. The first driving part includes a first electric push rod installed on the lower leg supporting structure 300. At this time, the first lead screw 304 may be replaced by a conventional rod, and a first sliding block instead of the first nut 31 is slidably sleeved on the rod. The first electric push rod is arranged in parallel with the rod, and the telescopic end of the first electric push rod is seemed to the first sliding block.

According to an embodiment of the present disclosure, it is also provided with a first distance adjusting mechanism for driving the tibia K-wire mounting structure 10 to move close to or away from the lower leg supporting structure 300.

According to an embodiment of the present disclosure, a first distance adjusting mechanism is formed by two first distance adjusting devices 40. The first distance adjusting mechanism is arranged perpendicular to the lower leg supporting structure 300, and is respectively arranged between the two first nuts 31 and the universal ball joint 003. The two first distance adjusting devices 40 are able to be driven individually, to make the tibia K-wire mounting structure 10 on the corresponding side to be movable close to or away from the lower leg supporting structure 300 and to be locked; and the two first distance adjusting devices 40 are also able to be driven simultaneously. The first distance adjusting device 40 may adopt an electric push rod.

When the tibia K-wire mounting structure 10 is secured to the first K-wire 11, since the distances from a position where the first K-wire 11 is implanted to the leg supporting structure 300 are different according to the patient's conditions, the first distance adjusting device 40 are able be driven individually, so that the two tibia K-wire mounting structures 10 correspond to and are secured to the both ends of the first K-wire 11.

After the tibia K-wire mounting structure 10 is secured to the first K-wire 11, when the tibia fracture has a pronation or valgus displacement, the two first distance adjusting devices 40 are driven individually to adjust the distance of the two ends of the first K-wire 11 protruding from the lower leg supporting structure 300, thereby correcting the pronation or valgus angle of the tibia fracture.

According to an embodiment of the present disclosure, it is also provided with a tibia proximal position adjusting device (i.e., a tibia fracture reduction mechanism). The tibia proximal position adjusting device includes at least one first jacking assembly that is arranged at a longitudinal centerline position of the lower leg supporting structure 300; at least two first lateral pressing assemblies that are respectively arranged on both sides of the lower leg supporting structure 300; and a binding band having one end secured to a first supporting pipe 305; and the other end detachably secured to another first supporting pipe 305, or is detachably secured to an original first supporting pipe 305 after being folded around the other first supporting pipe 305; and the length of the binding band around the patient's lower leg is adjustable.

The patient's lower leg is fixed by the binding band to ensure the stability of the operation.

According to an embodiment of the present disclosure, the first jacking assembly includes a lower leg fixing plate 51 with an inward concave radian, and having two ends connected with corresponding first supporting pipes 305; and a third electric push rod 52 fixed at the middle of the lower leg fixing plate 51, and having a telescopic end that protrudes from the lower leg fixing plate 51, and is secured to a top pressing plate, so as to ensure a top pressing area without damaging skin tissue. The pressing plate is preferably a hemisphere protruding toward the limb.

When the first jacking assembly is used to correct a tibia fracture displacement, the third electric push rod 52 is controlled to extend to squeeze the end of the tibia outwardly so as to correct a anterior angulation of the tibia fracture.

According to an embodiment of the present disclosure, the first jacking assembly further includes a second driving part 53 for driving the lower leg fixing plate 51 to be slidable along the first supporting pipes 305 and to be locked, so as to adjust a jacking position of the first jacking assembly and meet the operation requirements of different patients.

Specifically, the second driving part 53 includes an electric push rod, which is arranged in the direction of the first supporting pipe 305 and secured to the lower leg supporting structure 300. The telescopic end of the electric push rod is secured to the lower leg fixing plate 51, and both ends of the lower leg fixing plate 51 are slidably connected with the first supporting pipe 305. By extension or retraction of the electric push rod, the lower leg fixing plate 51 is driven to move the third electric push rod 52 up and down in the direction of the first supporting pipe 305.

According to an embodiment of the present disclosure, the first lateral pressing assembly includes two first sliding seats 54, a first passive telescopic part, a first active telescopic part 56 and a first linkage plate 57. The lower leg fixing plate 51 and the first linkage plate 57 may be the same plate body.

The two first sliding seats 54 are respectively arranged on the two first supporting pipes 305 and are slidably connected with the first supporting pipes 305. The first passive telescopic part is arranged transversely along the lower leg supporting structure 300 and secured to the first sliding seat 54. The first passive telescopic part includes a rod body 551 and a pipe body 552 slidably sleeved with the rod body 551. The first active telescopic part 56 is arranged transversely along the lower leg supporting structure 300 and secured to the other first sliding seat 54. The telescopic end of the first active telescopic part faces towards the first passive telescopic part. The first linkage plate 57 has a concave radian, and both ends of the first linkage plate 57 are turned out to form a connecting part 571. The protruding end of the first passive telescopic part and the telescopic end of the first active telescopic part 56 pass through the connecting part 571 and are secured to the connecting part 571. The ends of the first passive telescopic part and the first active telescopic part opposite to each other are secured to lateral pressing plates to increase the side pressing area without damaging the skin tissue. The lateral pressing plates are preferably hemispheres protruding towards the limb.

When the first top lateral pressing assembly is used to correct the tibia fracture displacement, the first active telescopic part 56 is extended, and the first linkage plate 57 moves towards the first passive telescopic part to push the first passive telescopic part to be retracted, so that the first active telescopic part 56 presses one side at the proximal end of the patient's tibia while no force is applied on the other side thereof. The first active telescopic part 56 retracts, and the first linkage plate 57 moves towards the first active telescopic part 56, to pull the first passive telescopic part to be extended, so that the first passive telescopic part presses against the other side at the proximal end of the patient's tibia. The side displacement of the tibia fracture can be corrected by using a first top lateral pressing assembly.

According to an embodiment of the present disclosure, the first active telescopic part 56 is driven by a lead screw nut. The first active telescopic part includes a second lead screw 562, which is arranged transversely along the lower leg supporting structure 300 and has an outer end connected with a second motor 561 secured to another first sliding seat 54; and a first threaded sleeve 563, which is threadedly connected to the other end of the second lead screw 562 and passed through the corresponding connecting part 571 and is secured to the connecting part 571. The first threaded sleeve is driven to reciprocate by the forward rotation or reverse rotation of the second motor 561, such that the extension or retraction of the first active telescopic part 56 can be realized.

According to another embodiment of the present disclosure, the first active telescopic part 56 is driven by a telescopic rod. The first active telescopic part 56 includes a fourth electric push rod, which is arranged transversely along the lower leg supporting structure 300 and secured to another first sliding seat 54. The telescopic end of the fourth electric push rod passes through the corresponding connecting part 571 and is secured to the connecting part 571. According to an embodiment of the present disclosure, the first lateral pressing assembly further includes a third driving part 58 for driving the first linkage plate 57 to be slidable along the first supporting pipes 305 and to be locked. In this way, the lateral pressing position of the first lateral pressing assembly can be adjusted to meet surgical requirements of different patients.

Specifically, the third driving parts 58 includes an electric push rod. The electric push rod is arranged in the direction of the first supporting pipe 305 and installed on the lower leg supporting structure 300. The telescopic end of electric push rod is secured to the first sliding seat 54. By the extension or retraction of the electric push rod, the first sliding seat 54 is driven to drive the first lateral pressing assembly to move up and down in the direction of the first supporting pipe 305.

When the automatic traction device is used to perform the tibia intramedullary nailing operation, the first lifting mechanism on the tibia distal position adjusting device, the first distance adjusting mechanism and the tibia proximal position adjusting device are selectively and cooperatively used, to correct the pronation and valgus angle, lateral angulation deformity and anteroposterior angulation deformity at the tibia distal end, and perform traction and stretch to align the tibia fracture and restore the length of lower limb, so as to improve quality of the intramedullary nailing operation, and facilitate postoperative recovery. The automatic adjustment of the various mechanisms can reduce the operation difficulty, simplify the operating steps and shorten the operation time.

According to an embodiment of the present disclosure, a second lifting mechanism is also provided for driving the femur position adjusting device to move up and down synchronously along the upper leg supporting structure 200 and to be locked.

According to an embodiment of the present disclosure, the second lifting mechanism includes two second lifting parts. The two second lifting parts are respectively arranged on two second supporting pipes 202 and connected with the corresponding femur K-wire mounting structures 20 through universal ball joints 003. The two second lifting parts are able be driven individually to make the two femur K-wire mounting structures 20 on the corresponding side to be movable along the second supporting pipes 202 and to be locked; and the two second lifting parts are also able to be driven simultaneously.

When the femur K-wire mounting structures 20 are secured to the second K-wires 25, the two second K-wires 25 are implanted in parallel, since implantation angles of the second K-wire 25 are different, it is not necessary to implant in a transverse direction of the upper leg supporting structure 200. Therefore, when the two tibia K-wire mounting structures 10 are secured to the ends of the corresponding first K-wires 25, the two second lifting parts are able be driven individually, so that the two tibia K-wire mounting structures 10 correspond to and are secured to both ends of the second K-wires 25.

After the femur K-wire mounting structures 20 are secured to the second K-wires 25, when the femur fracture has pronation or valgus displacement, the two second lifting parts are able be driven individually to adjust the relative distance from the two ends of the second K-wire 25 to the upper leg supporting structure 200, so as to correct the pronation or valgus angle of the femur distal fracture and restore the fractured bone that has been displaced.

When the lower limb length is restored, the two second lifting parts are also able to be driven simultaneously, to pull the second K-wire 25 to the femur distal end, reduce the fracture of the fractured bone and restore length of the lower limb.

According to an embodiment of the present disclosure, each of the second lifting parts includes a lifting arm 61, a fourth driving part 62, a connecting arm 63 and a mounting sleeve 64.

The lifting arm 61 is arranged in parallel with the second supporting pipe 202 and located at the upper end of the second supporting pipe 202. The fourth driving part is used for driving the lifting arm 61 to be movable up and down along the second supporting pipe 202 and to be locked. The connecting arm 63 and the lifting arm 61 are arranged at an angle and is connected with the upper end of the lifting arm 61. The mounting sleeve 64 is sleeved on the connecting arm 63. The two femur position adjusting devices are arranged along the length direction of the connecting arm 63. The femur K-wire mounting structures 20 are connected to the mounting sleeve 64 by means of the universal ball joints 003.

According to an embodiment of the present disclosure, the fourth driving part is driven by a lead screw nut. The fourth driving part includes a fourth lead screw 22, which is arranged in parallel with the lifting arm 61, and has a lower end connected with a fourth motor 22 secured to the second supporting pipe 202; and a nut 611, which is secured to the lifting arm 61 and is threadedly connected to the fourth lead screw 22. The nut 611 is driven to move up and down by the forward rotation or the reverse rotation of the fourth motor 22, so as to drive the lifting arm 61.

According to another embodiment of the present disclosure, the fourth driving part is driven by a telescopic rod. The fourth driving part includes a sixth electric push rod, which is arranged in parallel with the lifting arm 61 and is secured to the second supporting pipe 202. The telescopic end of the sixth electric push rod is secured to the lifting arm 61. The the lifting arm 61 is driven by extension or retraction of the sixth electric push rod.

According to an embodiment of the present disclosure, it is also provided with a second distance adjusting mechanism for driving the femur K-wire mounting structure 20 to move close to or away from the upper leg supporting structure 200 along the connecting arm 63.

According to an embodiment of the present disclosure, the second distance adjusting mechanism includes two automatic telescopic parts 70 that may be automatically controlled components such as electric push rods, air cylinders or oil cylinders. Each of the automatic telescopic parts 70 is installed on the connecting arm 63 along the direction of the connecting arm 63. The femur K-wire mounting structures 20 are rotationally connected with the mounting sleeves 64 through the universal ball joints. The two automatic telescopic parts 70 are able to be driven individually to drive the mounting sleeve 64 to slide along the connecting arm 63 on the corresponding side; and the two automatic telescopic parts 70 are also able to be driven simultaneously.

When the femur K-wire mounting structures 20 are secured to the second K-wire 25, since the distances from the positon where the second K-wire 25 is implanted to the upper leg supporting structures 200 are different according to the patient's conditions. The second and first distance adjusting devices are able to be driven individually, so that the two femur K-wire mounting structures 20 correspond to and are secured to the both ends of the second K-wire 25.

After the femur K-wire mounting structures 20 are secured to the second K-wire 25, when the femur fracture has lateral angulation deformity, the second and first distance adjusting devices are driven individually to adjust the relative heights of the two ends of the second K-wire 25, thereby correcting the lateral angulation displacement of the femur fracture.

According to an embodiment of the present disclosure, it is also provided with a femur fracture anterior-posterior angulation adjusting mechanism for adjusting the angle between the connecting arm 63 and the lifting arm 61. By adjusting the pitch angle of the connecting arm 63, the anterior-posterior angulation of the femur fracture may be corrected, so as to reset the displaced fracture.

According to an embodiment of the present disclosure, the femur fracture anterior-posterior angulation adjusting mechanism includes two fifth driving parts. The two fifth driving parts are respectively disposed at the free ends of the two connecting arms 63, for driving the connecting arms 63 to rotate along a hinge point with the lifting arm 61.

According to an embodiment of the present disclosure, each of the fifth driving parts is driven by a lead screw nut. The fifth driving part includes a fifth lead screw 24, which forms a triangle with the connecting arm 63 and the lifting arm 61 and has a lower end connected with a fifth motor 23 hinged with the upper leg supporting structure 200; and a second threaded sleeve 26, which is threadedly connected to an upper end of the fifth lead screw 24, wherein the upper end of the second threaded sleeve 26 is hinged with the free end of the connecting arm 63. By the forward rotation or the reverse rotation of the fourth motor, the second threaded sleeve 26 is screwed in or out, so as to adjust the pitch angle of the connecting arm 63.

According to an embodiment of the present disclosure, each of the fifth driving parts is driven by a telescopic rod. The fifth driving part includes an eighth electric push rod. The eighth electric push rod forms a triangle with the connecting arm 63 and the lifting arm 61, and has a lower end hinged with the leg supporting structure, and an upper end hinged with the free end of the connecting arm 63. By extension or retraction of the eighth electric push rod, the pitch angle of the connecting arm 63 is adjusted.

According to an embodiment of the present disclosure, it is also provided with a femur fracture reduction mechanism. The femur fracture reduction mechanism includes at least one second jacking assembly, which is arranged at a longitudinal centerline position of the upper leg supporting structure 200; and at least two second lateral pressing assemblies, which are respectively arranged on both sides of the upper leg supporting structure 200.

It is also provided with a binding band. The binding band has one end secured to a second supporting rod and the other end detachably secured to another second supporting rod, or is detachably secured to the original second supporting rod after being folded around the other second supporting rod. And the length of the binding band around the patient's upper leg is adjustable.

According to an embodiment of the present disclosure, the second jacking assembly includes: a upper leg fixing plate, which has an inward concave radian and has both ends slidably connected with the corresponding second supporting pipe 202; and a ninth electric push rod, which is fixed at the middle of the upper leg fixing plate and has a telescopic end protruding from the upper leg fixing plate and is provided with a top pressing plate, wherein the top pressing plate is preferably a hemispherical surface protruding toward the limb.

When that second jacking assembly is used to correct the displacement of the femur fracture, the ninth electric push rod is controlled to extend to squeeze the end of the tibia to move outwardly and the other end of the tibia to move inwardly, so as to adjust the anterior-posterior angulation of the tibia fracture.

According to an embodiment of the present disclosure, the second jacking assembly further includes a sixth driving part for driving the upper leg fixing plate to slide along the second supporting pipe 202 and to be locked, so as to adjust the jacking position of the second jacking assembly and meet the operation requirements of different patients.

Specifically, the fourth driving part includes a tenth electric push rod. The tenth electric push rod is arranged along the direction of the second supporting pipe 202 and secured to the upper leg supporting structure 200. The telescopic end of the tenth electric push rod is secured to the upper leg fixing plate. The both ends of the upper leg fixing plate are slidably connected with the second supporting pipe 202. By the expansion and retraction of the tenth electric push rod, the upper leg fixing plate is driven to move along the second supporting pipe 202.

According to an embodiment of the present disclosure, the second lateral pressing assembly includes two second sliding seats, a second passive telescopic part, a second active telescopic part and a second linkage plate. The upper leg fixing plate and the second linkage plate may be a plate body.

The two second sliding seats are respectively arranged on the two second supporting pipes 202 and are slidably connected with the second supporting pipes 202. A second passive telescopic part is arranged transversely along the upper leg supporting structure 200 and fixed on a second sliding seat. The second passive telescopic part includes a rod body 551 and a pipe body 552 slidably sleeved with the rod body 551. The second active telescopic part is arranged transversely along the upper leg supporting structure 200 and fixed on another second sliding seat. The telescopic end of the second active telescopic part faces towards the second passive telescopic part. The second linkage plate has an inward concave radian and two ends turned out to form a connecting part 571. The protruding end of the second passive telescopic part and the telescopic end of the second active telescopic part pass through the connecting part 571 and are secured to the connecting part 571. The ends of the second passive telescopic part and the second active telescopic part opposite to each other are fixed lateral pressing plates. The lateral pressing plates are preferably hemispherical surfaces protruding toward the limb.

When a second top lateral pressing assembly is used to correct the displacement of femur fracture, the second active telescopic part is extended, and the second linkage plate moves towards the second passive telescopic part to push the second passive telescopic part to be retracted, so that the second active telescopic part presses against one side of the patient's femur proximal end, and no force applied on the other side. The second active telescopic part retracts, and the second linkage plate moves towards the second active telescopic part, to pull the second passive telescopic part to be extended, so that the second passive telescopic part presses against the other side of the patient's femur proximal end. The second top lateral pressing assembly is used to correct the lateral angulation deformity of femur fracture.

According to an embodiment of the present disclosure, the second active telescopic part is driven by a lead screw nut or a telescopic rod. The driving structure and working principle of the second active telescopic part may be basically the same as that of the first active telescopic part, which will not be repeated herein.

According to an embodiment of the present disclosure, the second lateral pressing assembly further includes a seventh driving part for driving the second sliding seat to be slidable along the second supporting pipe 202 and to be locked, so as to adjust the lateral pressing position of the second lateral pressing assembly and meet the surgical requirements of different patients.

Specifically, the fifth driving part includes a twelfth electric push rod. The twelfth electric push rod is arranged along the direction of the second supporting pipe 202 and secured to the upper leg supporting structure 200. The telescopic end of the twelfth electric push rod is secured to the second sliding seat. By the extension or retraction of the twelfth electric push rod, the second sliding seat is driven to drive the second lateral pressing assembly to move along the second supporting pipe 202.

When the automatic traction device is used to perform the tibia intramedullary nailing operation, the second lifting mechanism on the femur distal position adjusting device, the second distance adjusting mechanism and the femur fracture anterior-posterior angulation adjusting mechanism and the femur fracture reduction mechanism are selectively and cooperatively used, to correct the pronation and valgus angles, lateral angulation deformity and anterior-posterior angulation deformity at the femur distal end, and perform traction and stretch to align the tibia fracture and restore the length of lower limb, so as to improve quality of the intramedullary nailing operation, and facilitate postoperative recovery. The automatic adjustment of the various mechanisms can reduce the operation difficulty, simplify the operating steps and shorten the operation time.

In the automatic traction device for a lower limb fracture osteosynthesis of the present disclosure, all of the electric push rod may be replaced by the automatic telescopic parts such as air cylinders or oil cylinders.

The preferred embodiments of tins disclosure are mentioned above, and any simple modification, deformation and equivalent substitution made by anyone according to the present disclosure will fail within the scope sought for protection in the present disclosure.

What is claimed is:

1. An automatic traction device for a lower limb fracture osteosynthesis, comprising:
    a chassis structure, having a first end portion and a second end portion opposite to each other;
    a lower leg supporting structure, having a first end portion and a second end portion opposite to each other, wherein the first end portion of the lower leg supporting structure is connected to the first end portion of the chassis structure;
    an upper leg supporting structure, having a first end portion and a second end portion opposite to each other, wherein the first end portion of the upper leg supporting structure is connected to the second end portion of the chassis structure, and the second end portion of the upper leg supporting structure is connected to the second end portion of the lower leg supporting structure;
    a tibia distal position adjusting device, for adjusting a position and an angle of a distal end of a tibia, arranged on the lower leg supporting structure and close to the first end portion of the lower leg supporting structure; and
    a tibia proximal position adjusting device, for adjusting a position and an angle of a proximal end of a tibia, arranged on the lower leg supporting structure and close to the second end portion of the lower leg supporting structure,
    wherein the chassis structure is a telescopic structure; the upper leg supporting structure is a telescopic structure; the lower leg supporting structure is a telescopic structure; the lower leg supporting structure is rotatably connected to the chassis structure; the lower leg supporting structure is rotatably connected to the upper leg supporting structure; and the upper leg supporting structure is rotatably connected to the chassis structure,
    wherein the lower leg supporting structure comprises:

a first transverse bar and a second transverse bar parallel to each other; and
two first longitudinal assemblies connected between the first transverse bar and the second transverse bar and parallel to each other, and each of the first longitudinal assemblies has a telescopic structure,
wherein each of the first longitudinal assemblies comprises:
a first motor hinged on the first transverse bar;
a first lead screw driven by the first motor;
a first supporting pipe having one end connected to the second transverse bar and the other end sleeved on the first lead screw; and
a first locking member on the first supporting pipe, for locking the first lead screw and the first locking member.

2. The automatic traction device according to claim 1, wherein the tibia distal position adjusting device comprises:
two first nuts respectively on the two first lead screws and matched with the first lead screws;
two first distance adjusting devices respectively on the two first nuts, wherein the first distance adjusting devices are perpendicular to the lower leg supporting structure;
two universal ball joints respectively on the two first distance adjusting devices;
two tibia K-wire mounting structures respectively on the two universal ball joints; and
a first K-wire between the two tibia K-wire mounting structures;
wherein the two first distance adjusting devices are used to adjust a distance between the first K-wire and the lower leg supporting structure.

3. The automatic traction device according to claim 1, wherein the tibia proximal position adjusting device comprises:
two first sliding seats slidably disposed on the two first supporting pipes;
two third driving parts respectively on the two first supporting pipes, for driving the first sliding seats to be slidable along the first supporting pipes and to be locked;
a first passive telescopic part arranged transversely along the lower leg supporting structure and fixed on one of the two first sliding seats;
a first active telescopic part arranged transversely along the lower leg supporting structure and fixed on the other of the two first sliding seats; and
a first linkage plate, having connecting parts formed by bending on both end portions, wherein a protruding end of the first passive telescopic part and a telescopic end of the first active telescopic part respectively penetrate through the connecting parts and are telescopic relative to the connecting parts.

4. The automatic traction device according to claim 3, wherein the first passive telescopic part comprises:
a pipe body fixed on one of the two first sliding seats; and
a rod body sleeved within the pipe body and being telescopic relative to the rod body, wherein one end of the rod body is arranged through the connecting part.

5. The automatic traction device according to claim 3, wherein the first active telescopic part is driven by a lead screw nut, and the first active telescopic part comprises:
a second motor on the first sliding seat;
a second lead screw arranged transversely along the lower leg supporting structure and driven by the second motor;
a first threaded sleeve threadedly fitted to the second lead screw and arranged through the connecting parts close to the first threaded sleeve; and
a locking member at an end portion of the second lead screw, for locking the second lead screw and the connecting parts.

6. The automatic traction device according to claim 3, wherein the first active telescopic part is driven by a telescopic rod, and the first active telescopic part comprises:
a fourth electric push rod arranged transversely along the lower leg supporting structure and on the other of the first sliding seats, wherein a telescopic end of the fourth electric push rod is arranged through the connecting parts close to the fourth electric push rod; and
a locking member at an end of the fourth electric push rod, for locking the fourth electric push rod and the connecting parts.

7. The automatic traction device according to claim 3, wherein the tibia proximal position adjusting device further comprises:
two second distance adjusting devices between one of the two first sliding seats and the first passive telescopic part, and between the other one of the two first sliding seats the first active telescopic part, respectively, wherein the second distance adjusting devices are perpendicular to the lower leg supporting structure and used for adjusting distance between the first passive telescopic part and the lower leg supporting structure, and distance between the first active telescopic part and the lower leg supporting structure, respectively.

8. The automatic traction device according to claim 3, wherein the tibia proximal position adjusting device further comprises:
at least one first jacking assembly, each of the first jacking assemblies including:
a lower leg fixing plate with two ends respectively connected to the two first supporting pipes; and
a third electric push rod in a middle of the lower leg fixing plate, wherein the third electric push rod extends and retracts in a direction perpendicular to the lower leg supporting structure.

9. The automatic traction device according to claim 8, wherein both ends of the lower leg fixing plate are slidably arranged on the two first supporting pipes, and the first jacking assembly further comprises:
a second driving part for driving the lower leg fixing plate to be slidable along the first supporting pipes and to be locked.

10. The automatic traction device according to claim 8, wherein a surface of the lower leg fixing plate comprised an arc-shaped portion; a surface of the first linkage plate comprises an arc-shaped portion; each of a protruding end of the third electric push rod, a protruding end of the first passive telescopic part and a protruding end of the first active telescopic part is provided with a pressing plate.

11. The automatic traction device according to claim 1, wherein the upper leg supporting structure comprises:
a third transverse bar parallel to the first transverse bar;
two second longitudinal assemblies connected between the third transverse bar and the first transverse bar and parallel to each other, wherein each of the second longitudinal assemblies has a telescopic structure.

12. The automatic traction device according to claim 11, wherein each of the second longitudinal assemblies comprises:
a third motor on the third transverse bar;
a third lead screw driven by the third motor; and a second supporting pipe having one end connected to the second transverse bar, and the other end sleeved on the third lead screw, wherein an inner surface of the second supporting pipe has threads matched with the third lead screw.

13. The automatic traction device according to claim 12, further comprising:
a second lifting mechanism on the upper leg supporting structure and lifting relative to the upper leg supporting structure;
a femur position adjusting device for adjusting a position and an angle of a femur, disposed on the upper leg supporting structure and close to the second end portion of the upper leg supporting structure.

14. The automatic traction device according to claim 13, wherein the second lifting mechanism comprises:
two fourth motors respectively on the two second supporting pipes;
two fourth lead screws respectively driven by the two fourth motors;
two lifting arms slidably disposed on the two second supporting pipes, respectively, wherein a nut matched with the fourth lead screw is provided at a lower end portion of the lifting arm.

15. The automatic traction device according to claim 14, wherein the second lifting mechanism further comprises:
two connecting arms with end portions respectively hinged to the upper end portions of the two lifting arms, wherein the two fourth lead screws are parallel to the two second supporting pipes, the two lifting arms are parallel to the two second supporting pipes; and the femur position adjusting device is arranged on the two connecting arms.

16. The automatic traction device according to claim 15, further comprising:
two fifth motors respectively hinged to the two fourth motors;
two fifth lead screws respectively driven by the two fifth motors; and
two second threaded sleeves having one end portions respectively matched with the two fifth lead screws, and the other end portions respectively hinged to the other end portions of the two connecting arms.

17. The automatic traction device according to claim 15, wherein the femur position adjusting device comprises:
two mounting sleeves slidably disposed on the two connecting arms, respectively;
two automatic telescopic parts respectively arranged on the two connecting arms, for driving the connecting arms to be movable and to be locked;
two universal ball joints respectively arranged on the two mounting sleeves;
at least one pair of femur K-wire mounting structures, wherein each pair of femur K-wire mounting structures are respectively mounted on the two universal ball joints, and a second K-wire is installed between each pair of the femur K-wire mounting structures;
wherein the automatic telescopic part is used to adjust a distance between the second K-wire and the upper leg supporting structure.

* * * * *